US006866742B2

(12) United States Patent
Hashiguchi et al.

(10) Patent No.: US 6,866,742 B2
(45) Date of Patent: Mar. 15, 2005

(54) ADHESIVE FOR SILICONE RUBBER LINING MATERIALS

(75) Inventors: Masanao Hashiguchi, Tokuyama (JP); Takaaki Imakura, Tokuyama (JP); Toshio Kawaguchi, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 10/399,500

(22) PCT Filed: Jul. 24, 2002

(86) PCT No.: PCT/JP02/07504

§ 371 (c)(1), (2), (4) Date: Aug. 4, 2003

(87) PCT Pub. No.: WO03/013443

PCT Pub. Date: Feb. 20, 2003

(65) Prior Publication Data

US 2004/0020597 A1 Feb. 5, 2004

(51) Int. Cl.$^7$ ........................ C09J 133/08; C09J 133/10
(52) U.S. Cl. .......................... 156/329; 528/31; 525/474
(58) Field of Search ........................... 156/329; 528/31; 525/474

(56) References Cited

U.S. PATENT DOCUMENTS 5,476,912 A * 12/1995 Hosoi et al. ................ 526/279
6,566,479 B1 * 5/2003 Bublewitz et al. ............ 528/15

FOREIGN PATENT DOCUMENTS

| | | | |
|---|---|---|---|
| JP | 02-043209 | | 2/1990 |
| JP | 04-068007 | | 3/1992 |
| JP | 05-025292 | | 2/1993 |
| JP | 07-070246 | | 3/1995 |
| JP | 07-076611 | | 3/1995 |
| JP | 2001-57988 | * | 3/2001 |
| WO | 99/37272 | * | 7/1999 |

* cited by examiner

*Primary Examiner*—Kuo-Liang Peng
(74) *Attorney, Agent, or Firm*—Sherman & Shalloway

(57) ABSTRACT

An adhesive for silicone rubber lining materials, for adhering a silicone rubber lining material and a (meth)acrylic resin denture base together, comprising (a) 100 parts by weight of an organic solvent, (b) 0.1 to 20 parts by weight of a (meth)acrylic polymer modified with a siloxane having a functional group reactive in the hydrosilylation reaction; and (c) 0.1 to 20 parts by weight of a polymer of a (meth)acrylic acid alkyl ester represented by the following formula, $CH_2{=}C(X){-}COOR$, wherein X is a hydrogen atom or a methyl group, and R is an alkyl group having 1 to 6 carbon atoms. This adhesive adheres the silicone rubber lining material and the (meth)acrylic resin denture base together very strongly. The adhering force is favorably maintained not only in the initial period but also for extended periods of time, offering excellent durability of adhesion. The initial adhering force and the durability of adhesion are also exhibited even by using a halogen-free organic solvent.

8 Claims, No Drawings

ADHESIVE FOR SILICONE RUBBER LINING MATERIALS

TECHNICAL FIELD

The present invention relates to an adhesive for lining materials for adhering a silicone rubber lining material with a denture base made of a (meth)acrylic resin. More specifically, the invention relates to an adhesive for silicone rubber lining materials, which can be suitably used when a halogen-free organic solvent is used as an organic solvent.

The invention further relates to a kit for lining a denture base made of a (meth)acrylic resin, comprising the above adhesive for the lining materials and a settable composition for the silicone rubber lining materials, and to a method of adhering the silicone rubber lining material and a (meth) acrylic denture base by using the adhesive for the lining materials.

BACKGROUND ART

A large proportion of patients who must be fitted with a denture and, particularly, with a full denture are aged persons. In general, further, the alveolar ridge shows such a large bone absorption that an increased force of occlusion must be born per a unit area. The alveolar ridge mucosa, too, becomes thin due to senile atrophy. Therefore, the shock due to occlusion and masticatory pressure is not relaxed but is directly transmitted to the alveolar bone. As a result, a thin mucosa sandwiched between the hard resin denture base and the hard alveolar bone is squeezed and gets scarred after every occlusion, and produces a pain.

In such a difficult case of disease, good results are not obtained for stably maintaining and supporting the denture even if the denture base is produced by using a commonly used (meth)acrylic resin only. Namely, it is necessary to line the surface of the denture base mucosa with a material having a suitable degree of elasticity, to compensate the lost viscoelasticity of the residual ridge mocusa and to impart cushioning property for relaxing the shock at the time of occlusion.

There has been favorably used a silicone rubber lining material of the room temperature vulcanizing type that cures at a temperature of up to 50° C. However, the silicone rubber lining material poorly adheres to the (meth)acrylic resin which is the denture base. Therefore, there have been developed several adhesives for adhering the (meth)acrylic resin which is the denture base with the silicone rubber material which is the lining material, and there has been known the one obtained by dissolving a particular acrylic copolymer having a silyl group in a suitable volatile organic solvent.

For example, there have been developed an acrylic copolymer using an alkyl (meth)acrylate and a (meth)acrylic acid dimethyl vinyl silylalkyl ester (Japanese Unexamined Patent Publication (Kokai) No. 43209/1990) and an acrylic copolymer using an alkyl (meth)acrylate and a (meth)acrylic acid dimethyl hydrogensilylalkyl ester (Japanese Unexamined Patent Publication (Kokai) No. 68007/1992).

They are used by applying soluble solvent solutions of the above resins onto the (meth)acrylic resin of the denture base followed by drying and, then, applying a room temperature vulcanizing (setting through the hydrosilylation reaction) silicone paste which is a dental lining material. During the setting and/or after the setting, however, they must be heated at about 80° C. for 20 to 30 minutes or longer to accomplish a sufficient degree of adhesion.

There have further been developed acrylic random copolymers modified with a silicone having a polyorganosiloxane group with an SiH reaction point on a side chain thereof (Japanese Patents Nos. 3105733 and 3107702). The adhesives using these particular acrylic random copolymers are useful being capable of considerably strongly adhering the acrylic resin which is the denture base and the silicone rubber material which is the lining material together at low temperatures of from about 20 to about 30° C. within several minutes.

However, it has been desired to further improve the adhering performance.

As the organic solvent for dissolving the above silicone-modified acrylic copolymers, in particular, there has been used a halogen-containing organic solvent and, chiefly, methylene chloride. Use of the above organic solvent helps exhibit excellent adhering performance.

In recent years, however, the halogen-containing organic solvents have been suspected of causing environmental disruption and toxicity. Though the truth has not yet been clarified, it is desired to avoid the use of halogen-containing organic solvents even in the dental materials.

Therefore, the adhesive is now using a halogen-free organic solvent such as ethyl acetate or ethyl methyl ketone to substitute for the halogen-containing organic solvent. In this case, the obtained adhesive exhibits excellent adhering force nearly equal to the halogen-containing organic solvent in the initial stage of adhesion accompanied, however, by such a defect that the adhering force greatly decreases with the passage of time lacking durability in the adhering force (durability of adhesion).

As the adhesive for the lining materials, further, there has further been known the one comprising the above silicone-modified acrylic copolymer and an organic solvent of a polymer of a particular (meth)acrylic acid ester having a carboxyl group for adhering the silicone rubber lining material and the metallic denture base (Japanese Unexamined Patent Publication (Kokai) No. 25292/1993). The above adhesive, however, is not still satisfactory for the use of adhesion since its adhering force to the (meth)acrylic resin denture base is not satisfactory.

DISCLOSURE OF THE INVENTION

It is an object of the present invention to provide an adhesive for silicone rubber lining materials, capable of firmly adhering the (meth)acrylic resin and the silicone rubber lining material together, and exhibiting excellent durability of adhesion.

Another object of the present invention is to provide an adhesive for silicone rubber lining materials, favorably exhibiting the above excellent adhering performance even when the organic solvent that is used is a halogen-free organic solvent.

A further object of the present invention is to provide a kit for lining a (meth)acrylic resin denture base, comprising the above adhesive for lining materials exhibiting excellent adhering performance and a settable composition for the silicone rubber lining materials.

A still further object of the present invention is to provide a method of adhering a silicone rubber lining material and a (meth)acrylic resin denture base together by using the above adhesive for the lining materials exhibiting excellent adhering performance.

According to the present invention, there is provided an adhesive for silicone rubber lining materials, for adhering a silicone rubber lining material and a (meth)acrylic resin denture base together, comprising:

(a) 100 parts by weight of an organic solvent;

(b) 0.1 to 20 parts by weight of a (meth)acrylic polymer modified with a siloxane having a functional group reactive in the hydrosilylation reaction (hereinafter abbreviated as reactive siloxane-modified (meth)acrylic polymer); and (c) 0.1 to 20 parts by weight of a polymer of a (meth)acrylic acid alkyl ester (hereinafter abbreviated as (meth)acrylic acid lower alkyl ester polymer) represented by the following formula, $$CH_2{=}C(X){-}COOR$$

wherein X is a hydrogen atom or a methyl group, and R is an alkyl group having 1 to 6 carbon atoms.

According to the present invention, there is further provided a kit for lining a (meth)acrylic resin denture base comprising (I) a setting composition for silicone rubber lining materials, an (II) the adhesive for the lining materials.

According to the present invention, there is further provided a method of adhering a silicone rubber lining material and a (meth)acrylic resin denture base together by adhering the silicone rubber lining material with the (meth)acrylic resin denture base together by using the adhesive for the lining materials.

BEST MODE FOR CARRYING OUT THE INVENTION

Adhesive for the Lining Materials

An adhesive for silicone rubber lining materials of the present invention is obtained by blending (a) an organic solvent with (b) a reactive siloxane-modified (meth)acrylic polymer and (c) a (meth)acrylic acid lower alkyl ester polymer.

This adhesive is capable of very strongly adhering the silicone rubber lining material and the (meth)acrylic resin denture base together, the adhering force being favorably maintained not only in the initial period only but also over an extended period of time, showing excellent durability of adhesion. Such a durability of adhesion is exhibited particularly by being blended with a (meth)acrylic acid lower alkyl ester polymer which is the component (c). That is, when not being blended with the component (c), a considerably good initial adhering force is obtained, which, however, does not last for extended periods of time, and the durability of adhesion decreases greatly.

Component (c):

The (meth)acrylic acid lower alkyl ester polymer which is the component (c) that is characteristic of the present invention is a polymer of a (meth)acrylic acid alkyl ester represented by the following formula, $$CH_2{=}C(X){-}COOR$$

wherein X is a hydrogen atom or a methyl group, and R is an alkyl group having 1 to 6 carbon atoms, offering such advantages that it dissolves well in an organic solvent, can be favorably applied as a homogeneous solution, exhibits good affinity to the (meth)acrylic resin of the denture base that is to be adhered, and helps increase the adhering strength to the resin as described above.

When the number of carbon atoms of the alkyl group (R) in the above formula is not smaller than 6, even the polymer of the (meth)acrylic acid alkyl ester dissolves poorly in the organic solvent, and exhibits decreased affinity to the (meth) acrylic resin which is the denture base to be adhered, causing a decrease in the durability of adhesion. Further, when a hydrophilic group such as carboxyl group is bonded as a substituent to the alkyl group (R), affinity decreases relative to the highly hydrophobic silicone rubber lining material that is to be adhered.

In the (meth)acrylic acid lower alkyl ester polymer which is the component (c) used in the invention, the alkyl group (R) in the formula has 1 to 6 carbon atoms, and is an unsubstituted alkyl group such as methyl group, ethyl group, propyl group, butyl group, pentyl group or hexyl group. Concrete examples of the polymer of the (meth)acrylic acid alkyl ester having such an alkyl group (R) include homopolymers such as methyl acrylate, methyl methacrylate (MMA), ethyl acrylate, ethyl methacrylate (EMA), propyl acrylate, propyl methacrylate, butyl acrylate, butyl methacrylate, hexyl acrylate and hexyl methacrylate, or copolymers thereof.

The (meth)acrylic acid lower alkyl ester polymer may further have any other copolymerizable monomer unit in small amounts in a range in which the effect of the invention is not impaired, which is generally not larger than 3% by mol and, preferably, not larger than 1% by mol. As such other copolymerizable monomers, there can be exemplified acrylonitrile, acrylamide, styrene, methyl styrene and α-methyl styrene.

Among the above (meth)acrylic acid lower alkyl ester polymers of the invention, it is desired to use a polymer of the (meth)acrylic acid alkyl ester having the alkyl group (R) with 1 to 4 carbon atoms and; most desirably, to use a polymer of the (meth)acrylic acid alkyl ester having the alkyl group (R) with 1 to 2 carbon atoms, such as a copolymer of methyl acrylate and ethyl acrylate, and a homopolymer of methyl methacrylate (MMA) and ethyl methacrylate (EMA).

Though there is no particular limitation, it is desired that the (meth)acrylic acid lower alkyl ester polymer (c) has a weight-average molecular weight in a range of from 10,000 to 2,000,000 and, particularly, from 100,000 to 1,000,000 from the standpoint of maintaining highly dissolving property in the organic solvent and uniform applicability of the adhesive.

The (meth)acrylic acid lower alkyl ester polymer is, in many cases, obtained by polymerizing a starting monomer in the presence of a peroxide. From the standpoint of preservation stability of the adhesive of the present invention, however, it is desired that the amount of the residual peroxide is not larger than 1.0% by weight.

In the present invention, the (meth)acrylic acid lower alkyl ester polymer which is the component (c) is blended in an amount of from 0.1 to 20 parts by weight per 100 parts by weight of the organic solvent which is the component (a). When the (meth)acrylic acid lower alkyl ester polymer is blended in an amount of smaller than 0.1 part by weight, durability of adhesion is not obtained to a sufficient degree. When the blending amount exceeds 20 parts by weight, on the other hand, the adhesive layer becomes too thick resulting in a decrease in the strength of adhesion. It is particularly desired that the (meth)acrylic acid lower alkyl ester polymer is blended in an amount of from 0.1 to 10 parts by weight for accomplishing a low viscosity and good operability.

Component (b):

In the present invention, the reactive siloxane-modified (meth)acrylic polymer which is the component (b) comprises a homopolymer or a copolymer of a derivative of the (meth)acrylic acid ((meth)acrylic acid monomer) to which is bonded, as a side chain, a siloxane group having a functional group reactive in the hydrosilylation reaction.

As the functional group reactive in the hydrosilylation reaction, there can be exemplified a functional group having an unsaturated carbon double bond at a terminal or an Si—H group. Among them, desired examples include vinyl group, allyl group and Si—H group. From the standpoint of reactivity, further, the Si—H group is more desired.

The siloxane group having the above reactive functional group is the one having at least one silicon-oxygen-silicon bond and is, usually, an organosiloxane group. It is desired that the siloxane group has the average number of repeating units of siloxane units such as organomonosiloxane groups or organodisiloxane groups of from 1 to 200 and, particularly, from 10 to 100.

In the reactive siloxane-modified (meth)acrylic polymer which is the component (b), it is desired that the siloxane group having a reactive functional group exists in an amount in a range of from 0.1 to 90% by mole and, preferably, from 1 to 50% by mol of the (meth)acrylic acid monomer unit that constitutes the (meth)acrylic polymer. It is further desired that the number of the reactive functional groups exiting in a unit of siloxane groups is from 1 to 100 and, preferably, from 3 to 100.

Concrete examples of the reactive siloxane-modified (meth)acrylic polymer include (meth)acrylic copolymers having a structural unit (α) represented by the following formula (1), having a structural unit (β) represented by the following formulas (2) and/or (2'), and having a structural unit (γ) represented by the following formula (3), (1)

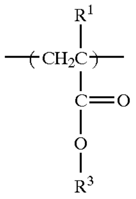

(2)

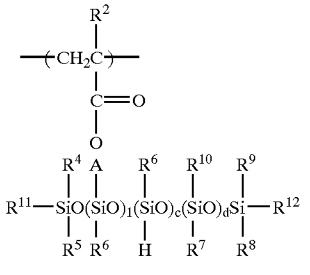

(2')

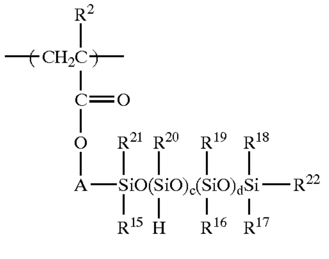

-continued (3)

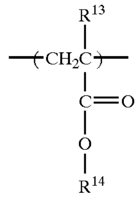

In the above formulas (1), (2), (2') and (3):

$R^1$, $R^2$ and $R^{13}$ are a hydrogen atom, a methyl group or an ethyl group;

$R^3$ is an alkyl group having 1 to 13 carbon atoms or an aryl group having 6 to 14 carbon atoms;

$R^4$ to $R^{10}$ and $R^{15}$ to $R^{21}$ are an alkyl group having 1 to 6 carbon atoms or an aryl group having 6 to 14 carbon atoms;

$R^{11}$, $R^{12}$ and $R^{22}$ are a hydrogen atom, an alkyl group having 1 to 6 carbon atoms or an aryl group having 6 to 14 carbon atoms;

$R^{14}$ is an unsaturated hydrocarbon group having 2 to 20 carbon atoms, which may have an ether bond or an ester bond in the main chain thereof;

A is a divalent hydrocarbon group having 2 to 20 carbon atoms, which may have an ether bond or an ester bond in the main chain thereof;

c and d are average number of repeating units, c being a number of from 1 to 100 and d being a number of from 0 to 100, and wherein $10 \leqq c+d \leqq 100$ and $0 \leqq d/c \leqq 10$.

In the above structural units (α), (β) and (γ), $R^1$, $R^2$ and $R^{13}$ in the formulas (1), (2), (2') and (3) are those selected from a hydrogen atom, a methyl group and an ethyl group, and are, desirably, hydrogen atoms or methyl groups from the standpoint of easily obtaining the raw materials, easy synthesis of a copolymer and, particularly, copolymerization reactivity of the starting monomer {(meth)acrylate compound}.

$R^3$ is an alkyl group having 1 to 13 carbon atoms, such as methyl group, ethyl group, n-propyl group, n-hexyl group, cyclohexyl group, n-octyl group or tridecyl group, or an aryl group having 6 to 14 carbon atoms, such as phenyl group, benzyl group or naphthyl group, and is, most desirably, a lower alkyl group having not more than 3 carbon atoms, such as methyl group, ethyl group or n-propyl group.

$R^4$ to $R^{10}$ and $R^{15}$ to $R^{21}$ are each an alkyl group having 1 to 6 carbon atoms, such as methyl group, ethyl group, n-propyl group or n-hexyl group, or an aryl group having 6 to 14 carbon atoms, such as phenyl group, benzyl group or naphthyl group, and is, desirably, a methyl group or a phenyl group from the standpoint of easy availability and synthesis of an organo(poly)siloxane having an SiH reaction point which is a starting material for synthesis.

$R^{11}$, $R^{12}$ and $R^{22}$ are a hydrogen atom, an alkyl group having 1 to 6 carbon atoms or an aryl group having 6 to 14 carbon atoms. Examples of the alkyl group and aryl group may be the same as those represented by $R^4$ to $R^{10}$. From the standpoint of synthesis of the organo(poly)siloxane having an SiH reaction point, which is the starting material, easy availability and reactivity of the obtained copolymer, however, it is desired that these groups ($R^{11}$, $R^{12}$ and $R^{22}$) are methyl groups or phenyl groups.

Further, $R^{14}$ is an unsaturated hydrocarbon group having 2 to 20 carbon atoms, such as vinyl group, allyl group, 1-butenyl group, 9-decenyl group, 2-(2-(2-(2-propenyloxy) ethoxy)ethoxy)ethyl group, 2-(3-butenoyloxy)ethyl group, or oleyl group.

A is a divalent hydrocarbon group having 2 to 20 carbon atoms, which may have an ether bond or an ester bond in the main chain thereof and is, desirably, a divalent hydrocarbon group having 3 to 10 carbon atoms, which may have an ether bond or an ester bond from the standpoint of easy synthesis. Concretely, there can be exemplified the following hydrocarbon groups, $-(CH_2)_3-$ $-(CH_2)_{10}-$ $-(CH_2CH_2O)_3-$ $CH_2CH_2CH_2-$

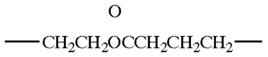

In the structural unit (β), c and d in the general formula (2) or (2') represent average numbers of repeating units of siloxane in the structural unit, and are selected from ranges that satisfy the following formulas:

$$1 \leq c \leq 100$$

$$0 \leq d \leq 100$$

$$10 \leq c+d \leq 100$$

$$0 \leq d/c \leq 13$$

From the standpoint of reactivity of the adhesive in the present invention, it is desired to so select c that the SiH groups are present in a number of not smaller than 3 on an average in one structural unit (β)

It is desired that the content of the structural units (α) in the (meth)acrylic copolymer used as the component (b) is in a range of from 10 to 99.9% by mol and, particularly, from 50 to 99.9% by mol, the content of the structural units (β) is from 90 to 0.1% by mole and, particularly, from 50 to 0.1% by mol, and the content of the structural units (γ) is from 0 to 89.9% by mole and, particularly, from 0 to 49.9% by mol. So far as being expressed by the above general formulas, each of the structural units (α), (β) and (γ) may be constituted not only by the units of a single kind but also by a plural kinds of units. When the content of the structural units (α) is smaller than the above range or when the contents of other structural units (β) and (γ) are larger than the above ranges, the ratio of the organo(poly)siloxane portion occupying the copolymer becomes great as compared to the (meth)acrylic polymer portion even when the molecular weight of the organo(poly)siloxane group is decreased in the structural unit (β). As a result, the adhesive poorly fits to the (meth)acrylic resin portion of the denture base and exhibits decreased adhering force. Further, when the content of the structural units (γ) is greater than the above range, unsaturated bonds existing in excess amounts impair the room temperature vulcanizing reaction (hydrosilylation setting reaction) of the silicone rubber lining material that is to be adhered, and the adhesive does not work to a sufficient degree. When the content of the structural units (β) is smaller than the above range, the ratio of the organo(poly) siloxane portion decreases in the copolymer, and the adhesive poorly fits to the silicone rubber of the lining material and is not adhered to the silicone rubber with a sufficiently large force.

The organo(poly)siloxane portion stands for an SiO skeletal portion having an organic group, and means a portion defined by $R^4$ to $R^{12}$ or $R^{15}$ to $R^{22}$, c and d in the formulas (2) and (2'). Further, the (meth)acrylic polymer portion stands for a poly(meth)acrylate skeletal portion other than the organo(poly)siloxane portion in the copolymer, and is defined by the number of the structural units (α), (β) and (γ), and by the ratio of the (meth)acrylic portion occupying the structural units (β).

It is desired that the (meth)acrylic copolymer used as the above component (b) has a weight-average molecular weight in a range of from 5,000 to 1,000,000. The values c and d in the formulas (2) and/or (2') representing the structural formula (β), the copolymer ratios of the structural units (α), (β) and (γ), and the total number of polymers, are determined so that the weight-average molecular weight lies within the above range. In the above copolymer, further, it is desired that the ratio of the molecular weight of the organo(poly)siloxane portion and the molecular weight of the (meth)acrylic polymer portion is selected to be 1:0.1 to 2 from the standpoint of compatibility of the acrylic resin of the denture base with the silicone rubber portion, reactivity and easy synthesis.

Described below are structures of structural units and the average number of repeating units of representative reactive siloxane-modified (meth)acrylic polymers used as the component (b).

In the following formulas, Ph denotes a phenyl group.

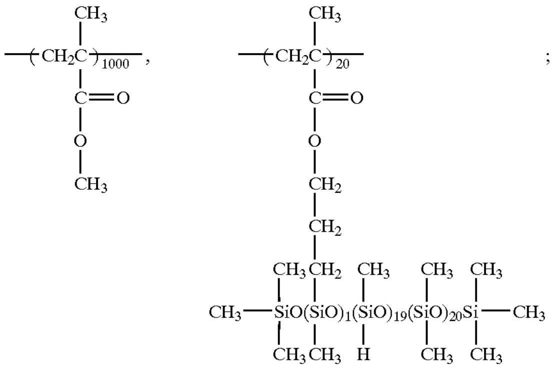

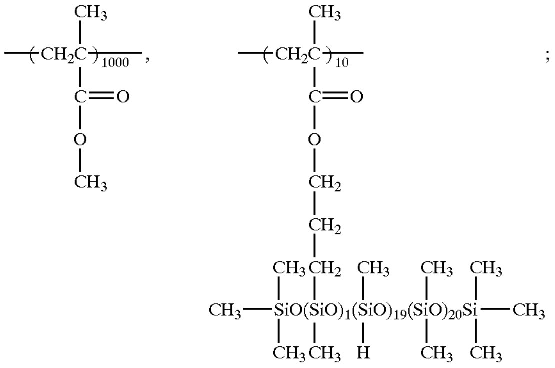

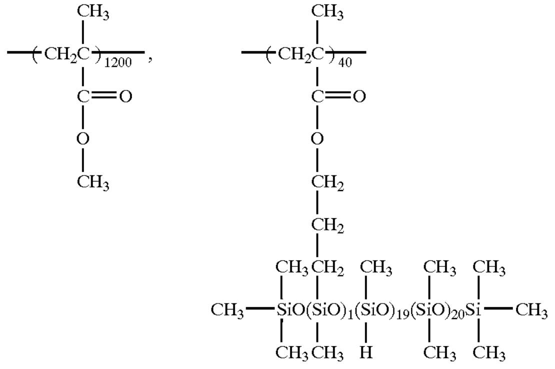

-continued
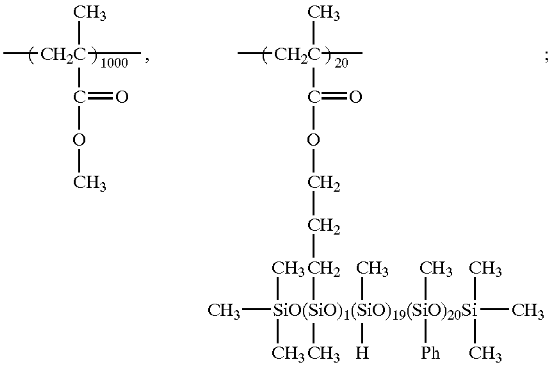
;
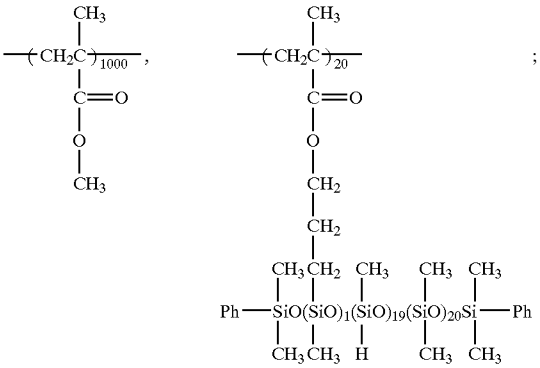
;
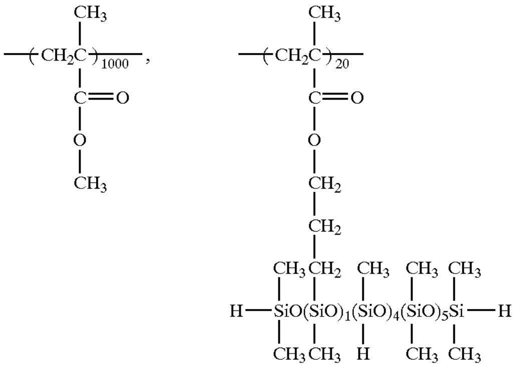
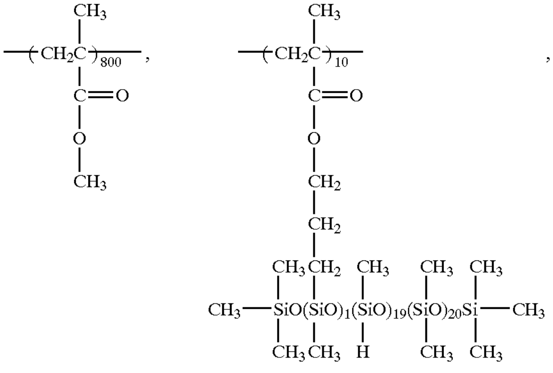
,
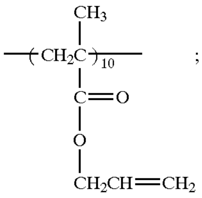
;
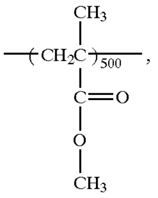
,
-continued
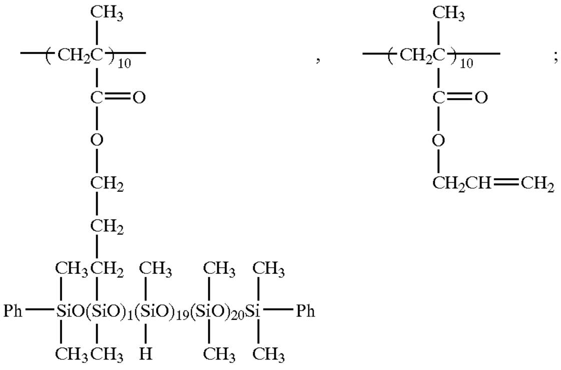
;
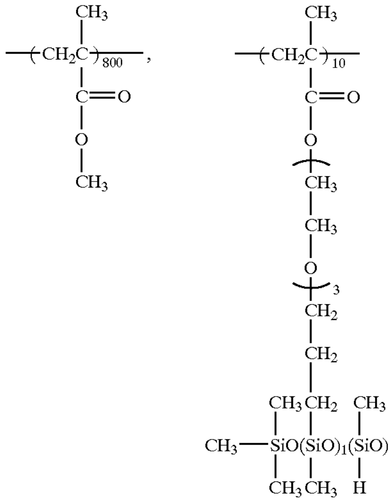
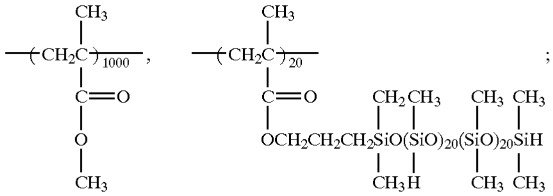
;
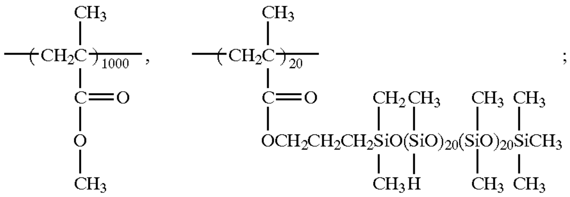
;
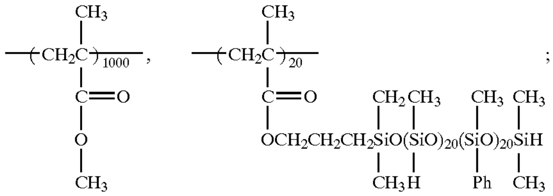
;
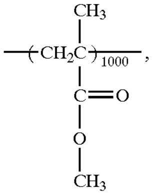

-continued

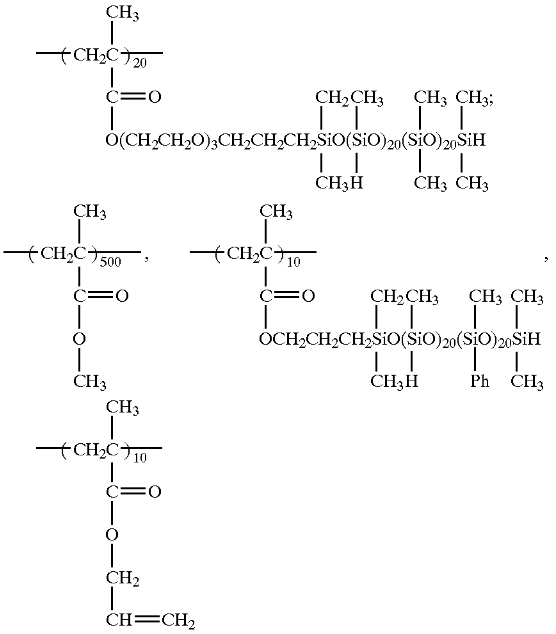

These copolymers are usually in the form of white powdery solids.

The order of bonding the structural units and the siloxane units in the above copolymers and the copolymers used in Examples and Comparative Examples appearing later, can be selected quite arbitrarily, and the numbers of repeating units in the structural formulas simply represent the structural units and average total amounts of the siloxane units.

There have heretofore been known the reactive siloxane-modified (meth)acrylic polymers comprising structural units (α) represented by the formula (1), structural units (β) represented by the formulas (2) and/or (2') and structural units (γ) represented by the formula (3), which can be produced in compliance with the methods taught in, for example, Japanese Patents Nos. 3105733 and 3107702.

The reactive siloxane-modified (meth)acrylic polymer which is the component (b) of the invention is blended in an amount of from 0.1 to 20 parts by weight per 100 parts by weight of the organic solvent (a). When the blending amount is smaller than 0.1 part by weight, the chemical bonding between the polymer and the silicone rubber lining material based on the hydrosilylation reaction is not sufficient, and a strong adhering force is not obtained. When the blending amount exceeds 20 parts by weight, the adhesive layer becomes so thick that the strength of adhesion decreases. It is desired that the blending amount is from 0.1 to 10 parts by weight to lower the viscosity and to obtain good operability.

Component (a):

There is no particular limitation on the organic solvent which is the component (a) used in the present invention provided it is capable of dissolving the polymers which are the components (b) and (c) described above, and it is allowable to use the halogen-containing organic solvents such as methylene chloride and chloroform that have heretofore been used chiefly for the adhesive for silicone rubber lining materials to a sufficient degree. In the present invention, however, it is desired to use a halogen-free organic solvent.

In recent years, it has been desired to use a halogen-free organic solvent as described above. However, the durability of adhesion decreases to a large extent between the silicone rubber lining material and the denture base. According to the present invention, on the other hand, despite the halogen-free organic solvent is used, it is made possible to effectively avoid a decrease in the durability of adhesion, which is a distinguished effect.

The halogen-free organic solvent is the one without having a halogen substituent in the molecular skeleton thereof, and its examples include hydrocarbon compounds such as hexane, heptane and pentane; aromatic compounds such as toluene and xylene; alcohol compounds such as ethanol, 1-propanol, 2-propanol, 1-butanol and 2-butanol; ether compounds such as diethyl ether, tetrahydrofurane and t-butyl methyl ether; ketone compounds such as acetone, methyl ethyl ketone and methyl isobutyl ketone; and ester compounds such as ethyl formate, methyl acetate, ethyl acetate, propyl acetate and isopropyl acetate.

According to the Council on Medicines No. 307, "Guideline of Residual Solvent in the Medicines" issued to urban and rural prefectures from the Ministry of Health and Welfare in 1998, the toxicity of the solvents remaining in the medicines has been classified into three classes. In the present invention, too, it is desired that the organic solvent that is used pertains to neither the Class 1 nor the Class 2 which are highly toxic, from the standpoint of safety. Among the halogen-free organic solvents, further, it is desired to use the one having a low boiling point and being volatile, since it dries quickly and is easy to handle. In particular, it is desired to use the one having a boiling point of from 20 to 150° C.

Because of these reasons, it is particularly desired to use ethyl acetate, acetone, ethyl methyl ketone or propyl acetate as the organic solvent (a) that is used in the present invention, and it is most desired to use ethyl acetate to obtain durability of adhesion. The halogen-free organic solvents may be used in a single kind or in a combination of two or more kinds. When used being mixed together in two or more kinds, it is desired that ethyl acetate is contained in an amount of not smaller than 50% by weight.

Other Components:

The adhesive of the present invention may contain additives such as a coloring agent, a perfume, etc. in addition to the above-mentioned components (a) to (c) within a range in which they do not impair the effect of the invention.

Preparation of the Adhesive:

The adhesive of the present invention can be easily prepared by dissolving the (meth)acrylic acid lower alkyl ester polymer (c) and the reactive siloxane-modified (meth) acrylic polymer (b) in the organic solvent (a).

Method of Using the Adhesive

There is no particular limitation on the method of use so far as the above adhesive of the present invention is used as an adhesive for adhering the denture base comprising chiefly the (meth)acrylic resin to the silicone rubber lining material. According to a representative method of operation, the adhesive is applied onto the (meth)acrylic resin of the denture base, the solvent is vaporized, and a silicone paste that sets through the hydrosilylation reaction, which is a silicone rubber lining material, is applied thereon so as to be set. The adhesive adheres to the (meth)acrylic resin simultaneously with the setting of the silicone paste that sets through the hydrosilylation reaction, and the adhesion is completed as the setting is completed.

Denture Base:

Here, the (meth)acrylic resin constituting the denture base is a homopolymer or a copolymer of a (meth)acrylic acid ester. Concretely speaking, there can be preferably used a homopolymer or a copolymer of a methyl (meth)acrylate or an ethyl (meth)acrylate.

Silicone Rubber Lining Material:

The silicone rubber lining material comprises a polymer of a compound (organopolysiloxane) having a siloxane bond as a main chain and, usually, exhibits a good flexibility. As the lining material having flexibility, there can be exemplified a soft lining material used chiefly for repairing an ill-fitted denture and a tissue conditioner used chiefly for the therapy for a short period of time (one week to several weeks) until the damaged oral mucosa recovers to a healthy state. Both of them can be adhered by using the adhesive of the present invention.

As the silicone rubber settable composition for obtaining the silicone rubber lining material, any known material used for such applications can be used without any limitation. The polymerization for curing may be of the heated setting type, condensation type, addition type or ultraviolet-ray curing type. It is, however, desired that the polymerization is of the room temperature addition polymerization type since it is capable of directly accomplishing the setting in the oral cavity of a patient without producing by by-products.

As the silicone rubber curable composition for the lining material of the room temperature addition polymerization type, there is desirably used a curable composition that contains, comprising;

(i) an organopolysiloxane having at least two organic groups in the molecules, the organic groups having a carbon-carbon unsaturated bond at the terminal;

(ii) an organohydrogenpolysiloxane having at least three SiH groups in the molecules;

(iii) a hydrosilylation catalyst; and (iv) a silicone resin filler material and/or a silica filler.

The settable composition for the silicone rubber lining material may further contain (v) an organohydrogenpolysiloxane having one or two SiH groups in the molecule to conduct the reaction. Upon being blended with this component (v), the modulus of elasticity tends to decrease and it becomes easy to adjust the viscoelasticity of the set body.

Details of the components used in the settable composition for silicone rubber lining materials have been disclosed in Japanese Unexamined Patent Publications (Kokai) Nos. 226613/1998 and 79020/2001, and the same components have also been used in the present invention.

For example, the organopolysiloxane which is the component (i) preferably used is represented by the following general formula,

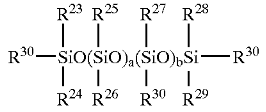

wherein a is an integer of from 400 to 1500, b is an integer of from 0 to 5, $R^{23}$ to $R^{29}$ are alkyl groups or aryl groups of the same kind or different kinds, and $R^{30}$ is an organic group (e.g., a vinyl group or an allyl group) having a carbon-carbon unsaturated bond.

Further, the organohydrogenpolysiloxane which is the component (ii) preferably used is represented by the following general formula,

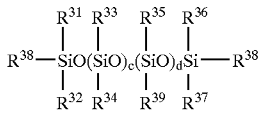

wherein c is an integer of from 1 to 100, d is an integer of from 3 to 50, $R^{31}$ to $R^{37}$ are alkyl groups or aryl groups of the same kind or different kinds, $R^{38}$ is an alkyl group, an aryl group or a hydrogen atom, and $R^{39}$ is a hydrogen atom.

Further, the organohydrogenpolysiloxane which is the component (v) preferably used is represented by the following general formula,

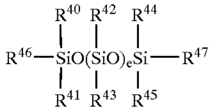

wherein e is an integer of from 1 to 100, $R^{40}$ to $R^{45}$ are alkyl groups or aryl groups of the same kind or different kinds, $R^{46}$ is an alkyl group, an aryl group or a hydrogen atom, and $R^{47}$ is a hydrogen atom.

As the hydrosilylation catalyst which is the component (iii), there can be preferably used a platinum catalyst such as a chloroplatinic acid, an alcohol-modified product thereof or a vinyl siloxane complex of platinum, or a similar rhodium catalyst.

It is desired that the silicone resin filler material used as the component (iv) has an average particle size in a range of from 0.1 to 100 μm and, particularly, from 0.1 to 20 μm. Concrete examples of the silicone resin filler include polymethylsilsesquioxane, poly(0.1 to 99.9% by mol of methyl+0.1 to 99.9% by mol of phenyl)silsesquioxne and poly(99 to 99.9% by mol of methyl+0.1 to 1% by mol of hydrogen)silsesqueoxane.

It is further desired that the silica filler used as the component (iv) has an average particle size of not larger than 10 μm and, particularly, in a range of from 0.001 to 1 μm. Concrete examples of the silica filler include pulverized quartz, molten silica powder, wet silica and fumed silica powder.

In the above curable composition, it is desired that the ratio of amounts of the component (i) and the component (ii) is such that the ratio of the total number of hydrogen atoms bonded to silicon atoms of the component (ii) to the total number of the carbon-carbon unsaturated bonds at the terminal of the siloxane chain of the component (i) is from 0.2 to 3.0 and, particularly, from 0.3 to 2.0.

When the component (v) is made present, further, it is desired that the components (i), (ii) and (v) are so combined together that the ratio of the total number of hydrogen atoms bonded to silicon atoms of the components (ii) and (v) to the total number of carbon-carbon unsaturated bonds at the terminals of the component (i), is from 0.5 to 5.0 and, particularly, from 0.7 to 5.0.

There is no particular limitation on the amount of blending the component (iii) provided the amount is enough for conducting the hydrosilylation reaction to a sufficient degree. When the platinum catalyst is used as the component (iii), in general, a preferred amount of blending the component (iii) is in a range of from 0.1 to 1000 ppm calculated as the amount of platinum with respect to the total amount of the components (i), (ii) and the component (v) that is blended as required.

The amount of the filler which is the component (iv) is adjusted at any time depending upon the properties (hardness, tensile strength, tearing strength, etc.) required for the set product that is obtained by setting the settable composition. Generally, however, it is desired that the filler which is the component (iv) is blended in an amount of from 1 to 30% by weight with respect to the total amount of the settable composition.

The settable composition for the silicone rubber lining materials is usually used in compliance with the so-called two-liquid mixing method. That is, the material A containing the setting catalyst and the material B without containing the setting catalyst (both of these materials are in the form of a liquid or a paste) are separately prepared and preserved. Just before the use, they are mixed together and are used for being set.

Here, the mixed material of the settable composition has a problem in the handling thereof; i.e., its viscosity is low at first and easily drips, so that applying the mixed one onto the denture becomes difficult. This tendency becomes more conspicuous in the case of the curable composition for obtaining a lining material for the tissue conditioner that requires a high degree of flexibility. If the mixed material easily drips, for example, the mixed material applied on the edges of the denture base flows out at the time of curing the curable composition (mixed material) in the oral cavity of a patient. As a result, the lining material obtained by the setting of the mixed material fails to assume a round shape which is necessary for the denture to be strongly adhered in the oral cavity.

In this case, blending a liquid polyether into the settable composition is effective for preventing the dripping while suppressing the viscosity of the mixed material of the curable composition. As the liquid polyether, there can be used any known compound which is in the liquid state or in the viscous state exhibiting at least fluidity at 25° C. in a single kind or in a combination of two or more kinds provided it does not impair the curing reaction of the organopolysiloxane.

What can be favorably used as the liquid polyether is a polyether having an alkylene oxide group as a repeating unit. As the alkylene oxide group, it is desired to use the one having a straight chain or branched chain alkylene group with 2 to 4 carbon atoms. For example, there can be preferably used polyalkylene glycols such as polyethylene glycol, polypropylene glycol, and polybutylene glycol; and polyethers in which the polyalkylene glycol is ether-bonded to the hydroxyl group of the glycerin. Among them, it is desired to use a polyalkylene glycol from the standpoint of its high drip-preventing effect and biocompatibility. It is desired to use a polyethylene glycol having a molecular weight of from 200 to 600 and, most desirably, to use a polypropylene glycol having a molecular weight of from 400 to 3500.

It is desired that the liquid polyether is blended in an amount of from 0.01 to 5% by weight and, particularly, from 0.03 to 3% by weight with respect to the total amount of the settable composition (total amount of the materials A and B inclusive of the liquid polyether). Even when the blending amount is greater than the above range, there is no improvement in the effect for preventing the dripping causing a disadvantage in economy. When the blending amount is smaller than the above range, on the other hand, the effect is not enough for preventing the dripping. The liquid polyether may be added to either the above material A or the material B, or to both the materials A and B, or may further be added at the time of mixing the materials A and B together.

It is further allowable to add a variety of fillers and a variety of additives to the curable composition for the silicone rubber lining materials in addition to those described above within a range in which they will not impair the properties of the cured product.

Kit for Lining

According to a preferred embodiment of the present invention, the adhesive for the silicone rubber lining materials is realized as a kit for lining the (meth)acrylic resin denture base in combination with the above-mentioned settable composition for the silicone rubber lining material.

The adhesive of the present invention is capable of firmly adhering the silicone rubber lining material to the (meth) acrylic resin of the denture base within short periods of time simultaneously with the setting of the settable composition for the silicone rubber lining material based on the hydrosilylation reaction. Though the mechanism of adhesion has not been clarified yet, the present inventors speculate it as described below.

Namely, the organic solvent in the adhesive causes the (meth)acrylic resin of denture base to swell, wherein the resin is impregnated with the poly(meth)acrylate portion of the reactive siloxane-modified (meth)acrylic polymer (component (b)) in the adhesive inducing molecular entanglement of the poly(meth)acrylate chain. The siloxane portion having a functional group reactive in the hydrosilylation reaction, on the other hand, emerges on the surface of the adhesive layer. Here, if the silicone paste (settable composition for the silicone rubber lining material) which is settable upon the hydrosilylation reaction, is applying thereon, they become very compatible with each other because of the same siloxane and, besides, a point of double bond reaction in the silicone paste reacts with the functional group, which is reactive in the hydrosilylation reaction, in the reactive siloxane-modified (meth)acrylic polymer. It is therefore considered that the (meth)acrylic resin of denture base and the adhesive layer firmly adhere together, and the adhesive layer and the silicone rubber lining material firmly adhere together.

As for the mechanism of greatly improving the durability of adhesion due to the presence of the (meth)acrylic acid lower alkyl ester polymer in the adhesive, the inventors speculate it as described below.

That is, the (meth)acrylic acid lower alkyl ester polymer which is the component (c) has a property of easily and molecularly entangling with the (meth)acrylic resin of denture base. Therefore, addition of the above polymer further assists the molecular entanglement of the (meth)acrylate chain in the adhesive layer with the (meth)acrylic resin of denture base, contributing to enhancing the durability of adhesion.

In general, further, the (meth)acrylic resin is less impregnated with a halogen-free organic solvent than with a halogen-containing organic solvent. Therefore, use of the halogen-free organic solvent as an organic solvent for the adhesive leaves the molecular entanglement small between the (meth)acrylic resin of denture base and the poly(meth) acrylate chain in the adhesive layer. Therefore, the durability of adhesion is low. By being blended with the (meth)acrylic acid lower alkyl ester polymer as described above, however, the above-mentioned phenomenon is improved and the effect of the invention is exhibited more conspicuously.

As described above, the adhesive for the silicone rubber lining material of the present invention is capable of firmly adhering the (meth)acrylic resin of denture base and the lining material together, and the adhering performance is not only such that the adhering force is high in the initial period but also that the durability of adhesion is excellently maintained.

When the organic solvent in the adhesive is a halogen-free organic solvent such as ethyl acetate, the durability of adhesion decreases greatly. According to the present invention, however, the above effect is exhibited very favorably even when the organic solvent is the halogen-free organic solvent. Thus, the present invention offers a lowly toxic adhesive without using halogen-containing organic solvent which involves problems in regard to safety.

EXAMPLES

The invention will now be concretely described by way of Examples to which only, however, the invention is in no way limited.

Described below are the materials used for the tests.

(a) Halogen-free Organic Solvents:

Ethyl acetate (Wako Junyaku Co., special grade)

Acetone (Wako Junyaku Co., special grade)

Heptane (Wako Junyaku Co., special grade)

Diethyl ether (Wako Junyaku Co., special grade, abbreviated as ether)

(b) Reactive Siloxane-modified (Meth)acrylic Polymer

The following copolymers were used.

Copolymer ①

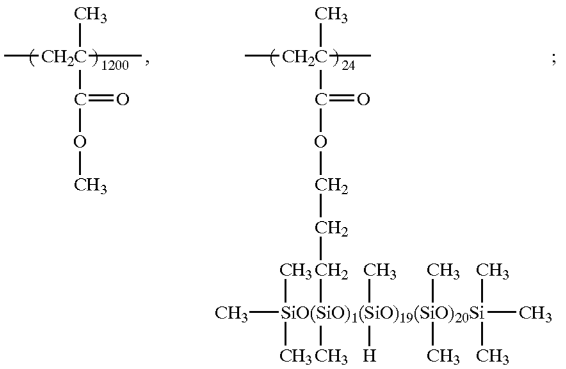

Copolymer ②

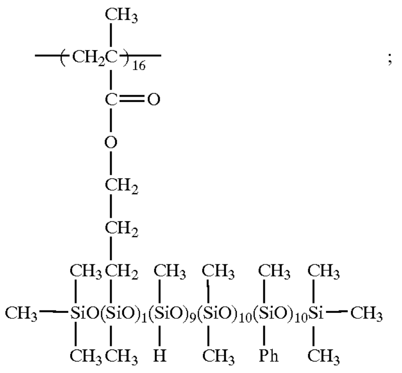

-continued

Copolymer ③

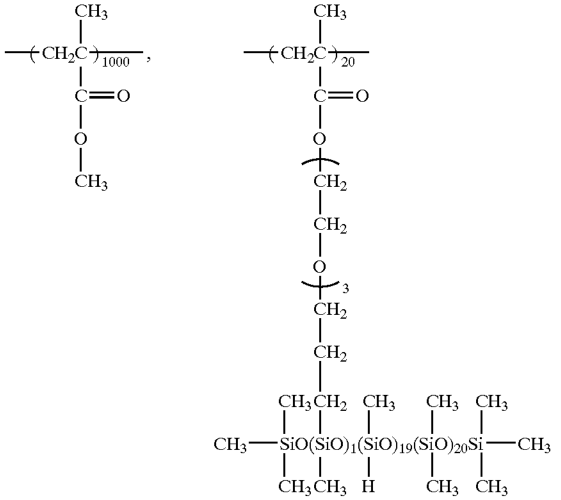

Copolymer ④

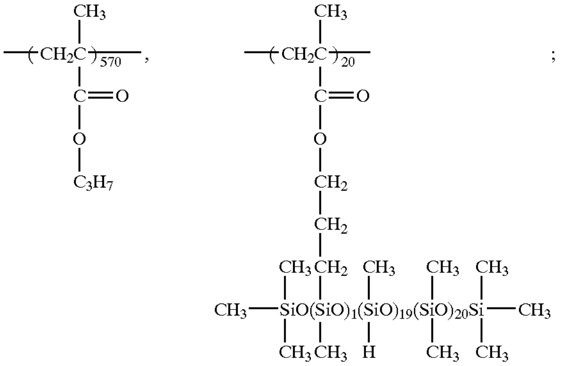

Copolymer ⑤

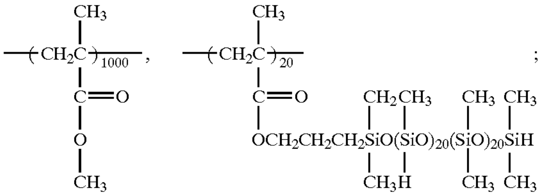

Copolymer ⑥

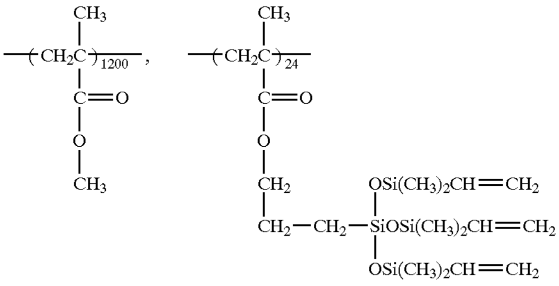

The above copolymers were synthesized by the methods described below.

Structures of the starting hydrogen siloxane compounds used for the synthesis of the copolymers are shown in Table 1 below.

TABLE 1

| Co-polymer | Starting hydrogen siloxane compound | Abbreviation |
|---|---|---|
| ① ③ ④ | 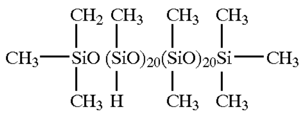 | DMS-M20H20: Shin-etsu kagaku |
| ② | 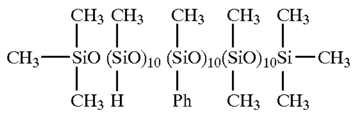 | DMS-M10H10P10 |
| ⑤ | 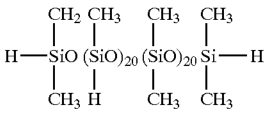 | DHS-M20H20 |

Synthesis of the Copolymer ①:

Into a flask were introduced 25 g of a methyl methacrylate, 0.63 g of an allyl methacrylate, 0.26 g of an azobisisobutyronitrile and 30 ml of toluene, which were, then, heated at 70° C. with stirring while being bubbled with nitrogen to obtain a copolymer (weight average molecular weight of 120,000) having a copolymer ratio of the methyl methacrylate and the allyl methacrylate of 50 to 1 (molar ratio).

Into a flask were introduced 27.7 g of a hydrogen siloxane compound DMS-M20H20 shown in Table 1, 300 ml of toluene and 0.33 g of a platinum/divinylsiloxane complex solution adjusted to 1000 ppm of platinum, which were, then, heated at 80° C. with stirring while being bubbled with nitrogen. 5 g of the copolymer (weight average molecular weight of 120,000) having a copolymer ratio of the methyl methacrylate and the allyl methacrylate of 50 to 1 (molar ratio) synthesized by the above method, was dissolved in 100 ml of toluene, which was then added thereto dropwise. After the dropwise addition has been finished, the mixture was heated and stirred for 6 hours. After the toluene was removed under reduced pressure, the excess of DMS-M20H20 was washed with a methanol/ethanol mixed solvent, separated by filtration and was dried to obtain the copolymer ①. The obtained polymer possessed a weight average molecular weight of 180,000 (calibrated with polystyrene).

Synthesis of the Copolymer ②:

Into a flask were introduced 25 g of a methyl methacrylate, 0.63 g of an allyl methacrylate, 0.40 g of an azobisisobutyronitrile and 30 ml of toluene, which were, then, heated at 70° C. with stirring while being bubbled with nitrogen to obtain a copolymer (weight average molecular weight of 80,000) having a copolymer ratio of the methyl methacrylate and the allyl methacrylate of 50 to 1 (molar ratio).

A copolymer ② was obtained by synthesizing a hydrogen siloxane compound DMS-M10H10P10 shown in Table 1 and the copolymer (weight-average molecular weight of 80,000) having a copolymer ratio of the methyl methacrylate and the allyl methacrylate of 50 to 1 (molar ratio) in the same manner as the synthesis of the copolymer ①.

Synthesis of the Copolymer ③:

Into a flask were introduced 25 g of a methyl methacrylate, 1.30 g of a methacrylic acid triethylene glycol monoarylether ester, 0.31 g of an azobisisobutyronitrile and 30 ml of toluene, which were, then, heated at 70° C. with stirring while being bubbled with nitrogen to obtain a copolymer (weight-average molecular weight of 100,000) having a copolymer ratio of the methyl methacrylate and the allyl methacrylate of 50 to 1 (molar ratio).

A copolymer ③ was obtained by synthesizing a hydrogen siloxane compound DMS-M20H20 shown in Table 1 and the copolymer (weight-average molecular weight of 100,000) having a copolymer ratio of the methyl methacrylate and the allyl methacrylate of 50 to 1 (molar ratio) in the same manner as the synthesis of the copolymer ①.

Synthesis of the Copolymer ④:

Into a flask were introduced 25 g of a methyl methacrylate, 1.1 g of an allyl methacrylate, 0.57 g of an azobisisobutyronitrile and 30 ml of toluene, which were, then, heated at 70° C. with stirring while being bubbled with nitrogen to obtain a copolymer (weight-average molecular weight of 60,000) having a copolymer ratio of the methyl methacrylate and the allyl methacrylate of 57 to 2 (molar ratio).

A copolymer ④ was obtained by synthesizing the hydrogen siloxane compound DMS-M20H20 and the copolymer (weight average molecular weight of 80,000) having a copolymer ratio of the methyl methacrylate and the allyl methacrylate of 57 to 2 (molar ratio) in the same manner as the synthesis of the copolymer ①.

Synthesis of the Copolymer ⑤:

A copolymer ⑤ was obtained by synthesizing the hydrogen siloxane compound DMS-M20H20 shown in Table 1 and the copolymer (weight average molecular weight of 100,000) having a copolymer ratio of the methyl methacrylate and the allyl methacrylate of 50 to 1 (molar ratio) obtained in the synthesis of the copolymer ③, in the same manner as the synthesis of the copolymer ①.

Synthesis of the Copolymer ⑥:

Into a flask were introduced 25 g of a methyl methacrylate, 2.3 g of a siloxane compound of the following formula,

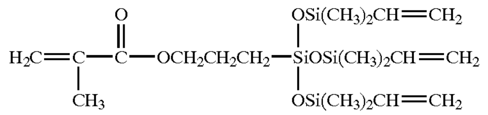

0.26 g of an azobisisobutyronitrile and 30 ml of toluene, which were, then, heated at 80° C. for 5 hours with stirring while being bubbled with nitrogen to obtain a copolymer ⑥.

(c) (Meth) Acrylic Acid Lower Alkyl Ester Polymer:

Polymethyl methacrylate (PMMA)

D250 ML (molecular weight, 250,000, Sekisui Kasei Co.)

MB100 (molecular weight, 800,000, Sekisui Kasei Co.)

Methyl methacrylate/ethyl methacrylate copolymer {P(MMA-EMA)}

MBE10-110 (copolymer ratio: EMA/MMA=10/90, molecular weight, 250,000, Sekisui Kasei Co.)

MBE70-55 L (copolymer ratio: EMA/MMA=70/30, molecular weight, 250,000, Sekisui Kasei Co.)

Polyethyl methacrylate (PEMA)

EMA35 (molecular weight, 500,000, Sekisui Kasei Co.)

In the following Examples and Comparative Examples, the addition-type silicone rubber used for the measurement of adhering strength was the one obtained by mixing the pastes A1 and A2, on the pasts B1 and B2 each in an equal amount followed by setting.

Paste A1:

Polydivinyldimethyl siloxane

ME91, Toshiba Silicone Co., 50 parts by weight

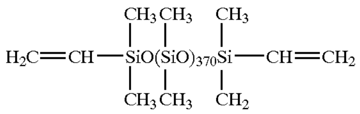

Polydivinyldimethyl siloxane

XC86-A9723, Toshiba Silicone Co., 50 parts by weight

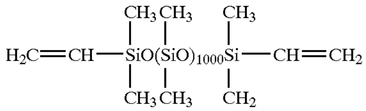

Platinum/vinyl siloxane complex solution (platinum, 1000 ppm, Pt/V2), 0.3 parts by weight Fine polymethylsilsesqueoxane particles (particle size, 3 μm, obtained by the hydrolysis of a methyltrimethoxysilane), 40 parts by weight Paste A2:

Polydivinyldimethyl siloxane

ME91, Toshiba Silicone Co., 50 parts by weight

Polydivinyldimethyl siloxane

XC86-A9723, Toshiba Silicone Co., 50 parts by weight

Polyhydrogenmethyl siloxane

DMS-M20H20, Shin-etsu Kagaku Co., 2 parts by weight

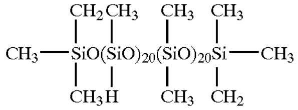

TSL9586, Toshiba Silicone Co., 7 parts by weight

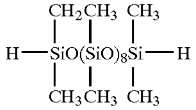

The silicone rubber obtained by mixing the above pastes A1 and A2 each in an equal amount followed by setting exhibited a tensile strength of about 2.0 MPa.

Paste B1:

Polydivinyldimethyl siloxane

ME91, Toshiba Silicone Co., 60 parts by weight

Polydivinyldimethyl siloxane

XC86-A9723, Toshiba Silicone Co., 40 parts by weight

Platinum/vinyl siloxane complex solution (platinum, 1000 ppm, Pt/V2), 0.3 parts by weight Silica powder (primary particle size, 0.01 μm, Reolosil MT-10, Tokuyama Co.), 10 parts by weight Polypropylene glycol (molecular weight, 3000, Wako Junyaku Co.), 0.1 part by weight Paste B2:

Polydivinyldimethyl siloxane

ME91, Toshiba Silicone Co., 40 parts by weight

Polydivinyldimethyl siloxane

XC86-A9723, Toshiba Silicone Co., 60 parts by weight

Polyhydrogenmethyl siloxane

DMS-M20H20, Shin-etsu Kagaku Co., 3 parts by weight

Silica powder (Reolosil MT-10, Tokuyama Co.), 10 parts by weight

Polypropylene glycol (Wako Junyaku Co.), 0.1 part by weight

The silicone rubber obtained by mixing the above pastes B1 and B2 each in an equal amount followed by setting exhibited a tensile strength of about 2 MPa.

Evaluation of adhering force and durability of adhesion, procedure for measurement, and the reference of evaluation were as described below.

(a) Evaluating the Adhering Force.

The adhesive solution prepared above was applied onto an acrylic plate (Acron GC) of which the surface was polished by using a water resistant polishing paper, #800, while pouring water thereon. The two pastes A1 and A2 or the two pastes B1 and B2 were taken each in an equal amount, mixed together well, and the mixed paste was applying on the acrylic plate on which the adhesive solution has been applied. The acrylic plate was left to stand at 25° C. for 10 minutes to cure the paste.

After setting, it was attempted to peel the acrylic plate and the set silicone rubber from the interface thereof by using a spatula. The manner of destruction at that moment was observed to evaluate the adhering force. The evaluation was rendered in four steps A to D in compliance with the following judgement:

A: Silicone rubber all underwent aggregation destruction (adhering force>2.0 MPa).

B: Mixed destruction of aggregation destruction and interfacial destruction (adhering force is nearly 2.0 MPa).

C: Interfacial destruction (adhering force<2.0 MPa).

D: Interfacial destruction (has not quite been adhered) (adhering force is almost 0 MPa).

(b) Evaluating the Durability of Adhesion.

There were prepared five samples for measuring the adhering strength after having been immersed in water maintained at 37° C. for 24 hours. The samples were subjected to a heat cycle testing at 4° C. and 60° C. repeated 10,000 times by using a heat shock tester (manufactured by Thomas Scientific Instrument Co.).

After put to the heat cycle testing, the samples were evaluated for their adhering force by the above method. The samples were evaluated to be ◎ when five pieces were all A, were evaluated to be ○ when four pieces were A and one piece was B, were evaluated to be Δ when two or more pieces were B and the remaining pieces were A, and were evaluated to be X when there were contained the pieces of C and D.

Example 1

To 100 parts by weight of an ethyl acetate (organic solvent) were added 1.5 parts by weight of a reactive siloxane-modified (meth)acrylic copolymer (copolymer ①) and 1.5 parts by weight of a (meth)acrylic acid lower alkyl ester polymer (D250 ML) to prepare an adhesive in the form of a solution of the present invention for silicone rubber lining materials.

As the addition-type silicone rubber, there were used the pastes A1 and A1.

By using the thus prepared adhesive, five pieces of the samples were evaluated for their adhering forces to find good initial adhering forces and good durability of adhesion as shown in Table 2.

Examples 2 to 17

Adhesives for the silicone rubber lining materials were prepared in the same manner as in Example 1 but using the compositions shown in Table 2, and were evaluated for their adhering forces and durability of adhesion. Good initial adhering force and good durability of adhesion were obtained no matter which adhesive was used for the silicone rubber lining material.

Comparative Example 1

A sample was prepared in the same manner as in Example 1 but using no adhesive for the silicone rubber lining material, and was evaluated for its adhering force and durability of adhesion. The result were as shown in Table 2. Quite no adhesion was accomplished in the initial stage and the durability testing could not be conducted.

Comparative Examples 2 to 8

Adhesives for the silicone rubber lining materials were prepared without adding the (meth)acrylic acid lower alkyl ester polymer but using the compounds shown in Table 2 instead of using the reactive siloxane-modified (meth) acrylic polymer, and were evaluated for their adhering forces and durability of adhesion in the same manner as in Example 1. The results were as shown in Table 2.

The initial adhering forces were good, but the durability of adhesion had been decreased to a conspicuous degree.

Comparative Examples 9 to 11

The adhering forces and durability of adhesion were evaluated in the same manner as in Example 1 by using copolymers (7), (8) and (9) having the following structures instead of using the (meth)acrylic acid lower alkyl ester polymer. The results were as shown in Table 2.

Copolymer (7)

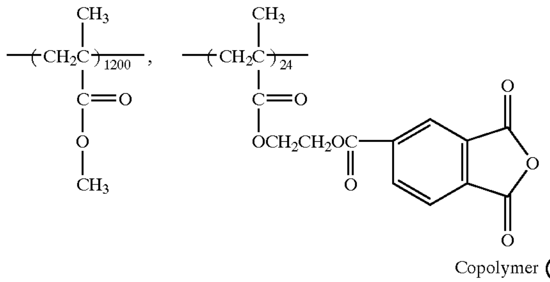

Copolymer (8)

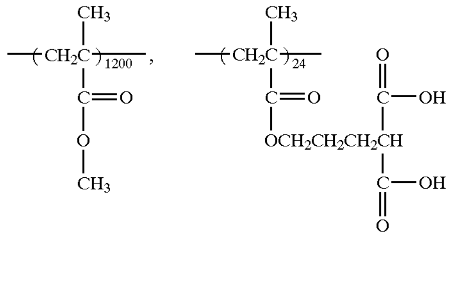

-continued

Copolymer (9)

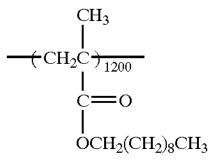

The initial adhering forces were good but the durability of adhesion was very poor.

Comparative Example 12

An adhesive for the silicone rubber lining material prepared without adding the reactive siloxane-modified (meth) acrylic polymer was evaluated for its adhesive force and durability of adhesion in the same manner as in Example 1. The results were as shown in Table 2.

Quite no adhesion was accomplished in the initial stage and the durability of adhesion could not be evaluated.

Comparative Example 13

As an example in which the blending amount of the (meth)acrylic acid lower alkyl ester polymer was smaller than the amount specified by the present invention, an adhesive for the silicone rubber lining material prepared by using the composition shown in Table 1 was evaluated for its adhering force and durability of adhesion in the same manner as in Example 1. The results were as shown in Table 2.

The initial adhering force was good but the durability of adhesion was very poor.

Comparative Example 14

An adhesive for the silicone rubber lining material prepared without adding the (meth)acrylic acid lower alkyl ester polymer but using the acetone as an organic solvent, was evaluated for its adhering force and the durability of adhesion in the same manner as in Example 1. The results were as shown in Table 2.

The initial adhering force was good but the durability of adhesion was very poor.

Comparative Example 15

An adhesive for the silicone rubber lining material prepared without adding the (meth)acrylic acid lower alkyl ester polymer but using the methylene chloride as an organic solvent, was evaluated for its adhering force and the durability of adhesion in the same manner as in Example 1. The results were as shown in Table 2.

The initial adhering force was good and the durability of adhesion was relatvely good but was slightly inferior to that of Example 1.

Examples 18 to 22

Adhesives for the silicone rubber lining materials were prepared in the same manner as in Example 1 but by using the pastes B1 and B2 as the addition-type silicone rubber, and were evaluated for their adhering forces and durability of adhesion. The results were as shown in Table 2. Good initial adhering forces and durability of adhesion were obtained no matter which adhesive was used for the silicon rubber lining material.

TABLE 2

| | Solvent | Siloxane non-modified polymer Kind | Siloxane non-modified polymer Concentration/ wt. parts | Siloxane modified copolymer Kind | Siloxane modified copolymer Concentration/ wt. parts | Adhering force | adhering force after heat shock test | Durability |
|---|---|---|---|---|---|---|---|---|
| Ex.1 | ethyl acetate | D250ML | 1.5 | copolymer ① | 1.5 | AAAAA | AAAAA | ◎ |
| Ex.2 | ethyl acetate | MB100 | 1.5 | copolymor ① | 1.5 | AAAAA | AAAAA | ◎ |
| Ex.3 | ethyl acetate | MBE10-110 | 1.5 | copolymer ① | 1.5 | AAAAA | AAAAA | ◎ |
| Ex.4 | ethyl acetate | MBE70-55L | 1.5 | copolymer ① | 1.5 | AAAAA | AAAAA | ◎ |
| Ex.5 | ethyl acetate | EMA35 | 1.5 | copolymer ① | 1.5 | AAAAA | AAAAA | ◎ |
| Ex.6 | ethyl acetate | EMA35 | 0.3 | copolymer ① | 1.5 | AAAAA | AAAAA | ◎ |
| Ex.7 | ethyl acetate | EMA35 | 4.0 | copolymer ① | 4.0 | AAAAA | AAAAA | ◎ |
| Ex.8 | ethyl acetate | EMA35 | 10.0 | copolymer ① | 2.0 | AAAAA | AAAAA | ◎ |
| Ex.9 | ethyl acetate | EMA35 | 1.5 | copolymer ② | 1.5 | AAAAA | AAAAA | ◎ |
| Ex.10 | ethyl acetate | EMA35 | 1.5 | copolymer ③ | 1.5 | AAAAA | AAAAA | ◎ |
| Ex.11 | ethyl acetate | EMA35 | 1.5 | copolymer ④ | 1.5 | AAAAA | AAAAA | ◎ |
| Ex.12 | ethyl acetate | EMA35 | 1.5 | copolymer ⑤ | 1.5 | AAAAA | AAAAA | ◎ |
| Ex.13 | ethyl acetate | EMA35 | 1.5 | copolymer ⑥ | 1.5 | AAAAA | AAAAA | ◎ |
| Ex.14 | ether | EMA35 | 1.5 | copolymer ① | 1.5 | AAAAA | AAAAB | ○ |
| Ex.15 | ethylmethyl ketone | EMA35 | 1.5 | copolymer ① | 1.5 | AAAAA | AAAAB | ○ |
| Ex.16 | acetone | EMA35 | 1.5 | copolymer ① | 1.5 | AAAAA | AAAAB | ○ |
| Ex.17 | ethyl acetate/ acetone (80/20) | EMA35 | 1.5 | copolymer ① | 1.5 | AAAAA | AAAAB | ○ |
| Ex.18 | ethyl acetate | EMA35 | 1.5 | copolymer ① | 1.5 | AAAAA | AAAAA | ◎ |
| Ex.19 | ethyl acetate | EMA35 | 0.3 | copolymer ① | 1.5 | AAAAA | AAAAA | ◎ |
| Ex.20 | ethyl acetate | EMA35 | 10.0 | copolymer ① | 2.0 | AAAAA | AAAAA | ◎ |
| Ex.21 | ethyl acetate | MBE10-110 | 1.5 | copolymer ① | 1.5 | AAAAA | AAAAA | ◎ |
| Ex.22 | ethyl acetate | EMA35 | 1.5 | copolymer ④ | 1.5 | AAAAA | AAAAA | ◎ |
| Comp.Ex.1 | — | — | — | — | — | DDDDD | — | X |
| Comp.Ex.2 | ethyl acetate | — | — | copolymer ① | 1.5 | AAAAA | BCCCC | X |
| Comp.Ex.3 | ethyl acetate | — | — | copolymer ② | 1.5 | AAAAA | BBCCC | X |
| Comp.Ex.4 | ethyl acetate | — | — | copolymer ③ | 1.5 | AAAAA | BBCCC | X |
| Comp.Ex.5 | ethyl acetate | — | — | copolymer ④ | 1.5 | AAAAA | BCCCC | X |
| Comp.Ex.6 | ethyl acetate | — | — | copolymer ⑤ | 1.5 | AAAAA | BCCCC | X |
| Comp.Ex.7 | ethyl acetate | — | — | copolymer ⑥ | 1.5 | AAAAA | BBBCC | X |
| Comp.Ex.8 | ethyl acetate | — | — | copolymer ① | 4.0 | AAAAA | BBCCC | X |
| Comp.Ex.9 | ethyl acetate | copolymer ⑦ | 1.5 | copolymer ① | 1.5 | AAAAA | BBCCC | X |
| Comp.Ex.10 | ethyl acetate | copolymer ⑧ | 1.5 | copolymer ① | 1.5 | AAAAA | BCCCC | X |
| Comp.Ex.11 | ethyl acetate | polymer ⑨ | 1.5 | copolymer ① | 1.5 | AAAAA | BBBCC | X |
| Comp.Ex.12 | ethyl acetate | EMA35 | 1.5 | — | — | DDDDD | — | X |
| Comp.Ex.13 | ethyl acetate | EMA35 | 0.05 | copolymer ① | 1.5 | AAAAA | BBBBC | X |
| Comp.Ex.14 | acetone | | | copolymer ① | 1.5 | AAAAA | CCCCC | X |
| Comp.Ex.15 | methylene chloride | — | — | copolymer ① | 1.5 | AAAAA | AAABB | ○ |

What is claimed is:

1. An adhesive for silicone rubber lining materials, for adhering a silicone rubber lining material and a (meth) acrylic resin denture base together, comprising:

(a) 100 parts by weight of an organic solvent;

(b) 0.1 to 20 parts by weight of a (meth)acrylic polymer modified with a siloxane having a functional group reactive in the hydrosilylation reaction; and (c) 0.1 to 20 parts by weight of a polymer of a (meth) acrylic acid alkyl ester represented by the following formula, $$CH_2{=}C(X){-}COOR$$

wherein X is a hydrogen atom or a methyl group, and

R is an alkyl group having 1 to 6 carbon atoms.

2. An adhesive for silicone rubber lining materials according to claim 1, wherein the (meth)acrylic resin polymer which is the component (b) contains structural units (α) represented by the following formula (1) in an amount of from 10 to 99.9% by mol, structural units (β) represented by the following formulas (2) and/or (2') in an amount of from 90 to 0.1% by mol, and structural units (γ) represented by the following formula (3) in an amount of from 0 to 89.9% by mol, and has a weight-average molecular weight of from 5,000 to 1,000,000, (1)

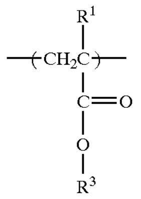

(2)

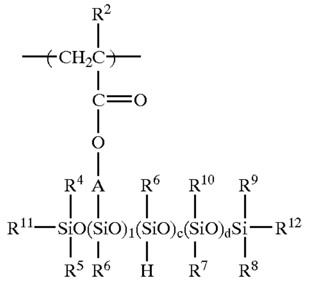

-continued (2')

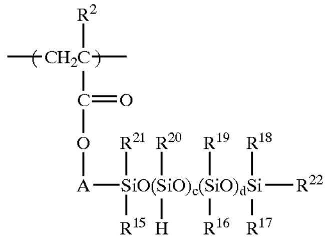

(3)

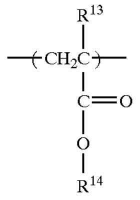

wherein, in the above formulas (1), (2), (2') and (3):

$R^1$, $R^2$ and $R^{13}$ are a hydrogen atom, a methyl group or an ethyl group;

$R^3$ is an alkyl group having 1 to 13 carbon atoms or an aryl group having 6 to 14 carbon atoms;

$R^4$ to $R^{10}$ and $R^{15}$ to $R^{21}$ are an alkyl group having 1 to 6 carbon atoms or an aryl group having 6 to 14 carbon atoms;

$R^{11}$, $R^{12}$ and $R^{22}$ are a hydrogen atom, an alkyl group having 1 to 6 carbon atoms or an aryl group having 6 to 14 carbon atoms;

$R^{14}$ is an unsaturated hydrocarbon group having 2 to 20 carbon atoms, which may have an ether bond or an ester bond in the main chain thereof;

A is a divalent hydrocarbon group having 2 to 20 carbon atoms, which may have an ether bond or an ester bond in the main chain thereof;

c and d are the average number of repeating units of silicone, c being a number of from 1 to 100 and d being a number of from 0 to 100, and wherein $10 \leqq c+d \leqq 100$ and $0 \leqq d/c \leqq 10$.

3. An adhesive for silicone rubber lining materials according to claim 1, wherein the organic solvent which is the component (a) is a halogen-free organic solvent.

4. An adhesive for silicone rubber lining materials according to claim 3, wherein the halogen-free organic solvent is ethyl acetate.

5. A kit for lining a (meth)acrylic resin denture base comprising (I) a setting composition for silicone rubber lining materials, and (II) the adhesive for the silicone rubber lining materials of claim 1.

6. A kit for lining a (meth)acrylic resin denture base according to claim 5, wherein the settable composition for silicone rubber lining materials, which is the component (I) contains:

(i) an organopolysiloxane having at least two organic groups in the molecules, the organic groups having a carbon-carbon unsaturated bond at the terminals;

(ii) an organohydrogenpolysiloxane having at least three SiH groups in the molecules;

(iii) a hydrosilylation catalyst; and (iv) a settable composition containing a silicone resin filler material and/or a silica filler.

7. A kit for lining a (meth)acrylic resin denture base according to claim 6, wherein the settable composition for silicone rubber lining materials, which is the component (I), further contains (v) an organohydrogenpolysiloxane having one or two SiH groups in the molecules thereof.

8. A method of adhering a silicone rubber lining material and a (meth)acrylic resin denture base together by adhering the silicone rubber lining material and the (meth)acrylic resin denture base together by using the adhesive for silicone rubber lining materials of claim 1.

* * * * *